United States Patent [19]
Nacci et al.

[11] Patent Number: 5,176,640
[45] Date of Patent: Jan. 5, 1993

[54] HYPODERMIC INJECTION SYRINGE PROVIDED WITH A PLUNGER ABLE TO RETRACT AND CONTAIN THE HYPODERMIC NEEDLE AFTER USE

[76] Inventors: Gaetano Nacci; Carla Nacci Tagliaferri, both of Via delle Fonti, 17, 50012 Bagno A Ripoli (Prov. of Florence), Italy

[21] Appl. No.: 752,533
[22] PCT Filed: Jan. 4, 1991
[86] PCT No.: PCT/EP91/00005
§ 371 Date: Sep. 6, 1991
§ 102(e) Date: Sep. 6, 1991
[87] PCT Pub. No.: WO91/10461
PCT Pub. Date: Jul. 25, 1991

[30] Foreign Application Priority Data
Jan. 9, 1990 [IT] Italy ......................................... 19028

[51] Int. Cl.⁵ .............................................. A61M 5/00
[52] U.S. Cl. .................................... 604/110; 604/195
[58] Field of Search ................ 604/110, 195, 198, 164, 604/218, 118

[56] References Cited

U.S. PATENT DOCUMENTS 4,772,265 9/1988 Walter .................................. 604/164
5,049,133 9/1991 Pascual ................................ 604/110

FOREIGN PATENT DOCUMENTS

WO89/00435 1/1989 PCT Int'l Appl. .
WO89/09075 10/1989 PCT Int'l Appl. .

Primary Examiner—John D. Yasko

[57] ABSTRACT

A syringe is provided with an engagement device which at the end of the plunger travel becomes connected to the hypodermic needle and to a pneumatic actuator, preferably of vacuum type, arranged to cause the needle to enter an appropriate chamber in the plunger after use.

17 Claims, 3 Drawing Sheets

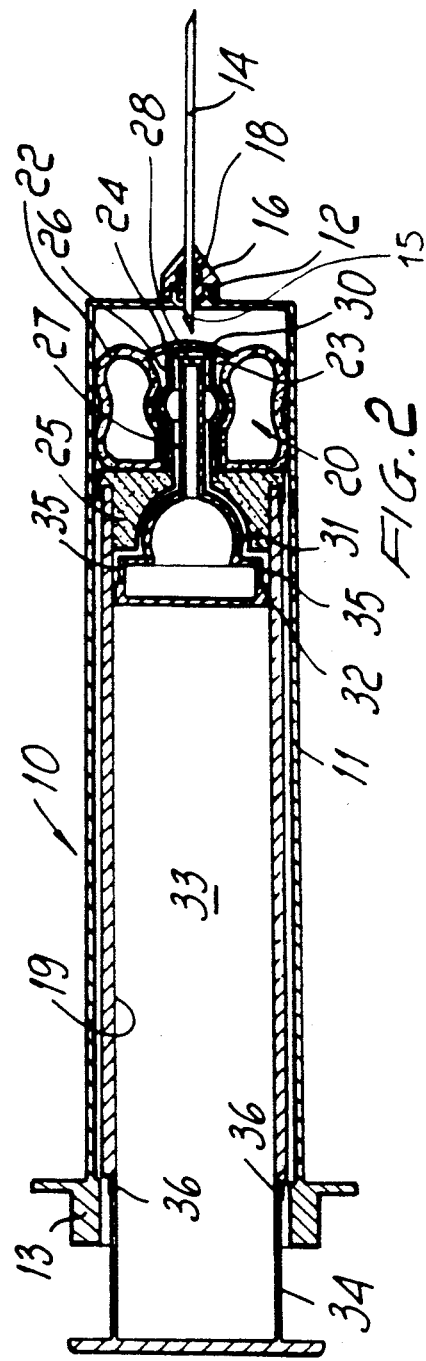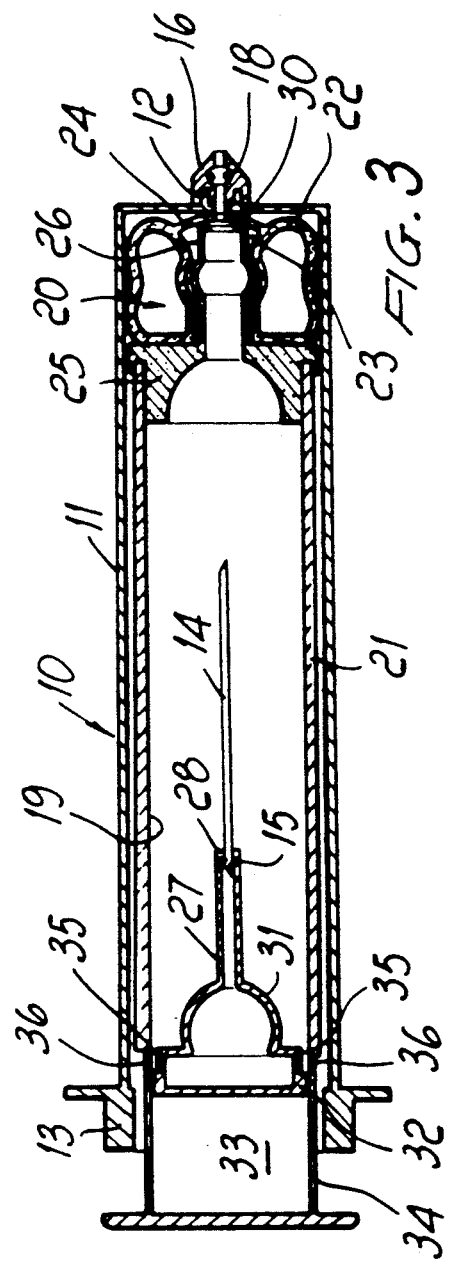

5,176,640

HYPODERMIC INJECTION SYRINGE PROVIDED WITH A PLUNGER ABLE TO RETRACT AND CONTAIN THE HYPODERMIC NEEDLE AFTER USE

FIELD OF THE INVENTION

This invention relates to a syringe provided with an engagement device able to cause the hypodermic needle to enter a cavity in the plunger shaft when the injection has been completed.

STATE OF THE ART

The problem of making a hypodermic syringe needle innocuous is currently important because of the serious problems of infection connected with accidental pricking with used and thus infected syringe needles. This problem which is exacerbated because many syringes designed for once-only use can in fact be used more than once.

Italian patent application No. 9543 A/88 of the present applicants describes a syringe in which, after use, the needle is made to enter a cavity in the plunger by means of a tension spring, one end of which is fixed to the inner surface of the plunger and which becomes operationally connected to a support member provided with a pawl able to engage the needle at the end of the plunger stroke and to pull it into said cavity.

Although effective, this device has certain constructional problems which make it difficult to implement in that the tension spring has to be fixed to the interior of the plunger, as stated.

SUMMARY OF THE INVENTION

The present invention enables a similar result to be obtained in a manner which considerably simplifies the construction and/or assembly of the syringe.

The syringe according to the present invention is formed from a cylindrical body, a plunger slidable within said cylindrical body and provided with a hollow shaft defining an inner chamber, and a hollow needle or metal cannula connected to said cylindrical body by first means which shear under a determined load, said syringe being characterised by comprising an engagement device which is connected to said plunger by second means which shear under a determined load at the end of travel of said plunger, and becomes operationally connected at the end of travel of the plunger to said needle and to a pneumatic actuator able to cause said needle to enter said chamber in the shaft of said plunger.

According to a preferred embodiment said pneumatic actuator is of the vacuum type, said plunger advantageously being provided with a hollow shaft defining an inner chamber in which vacuum is created and in which a piston rigid with said engagement device is slidable under sealed conditions.

With the proposed arrangement the syringe construction is simplified and its performance and reliability are optimized.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

These and further advantages and innovative and operational characteristics of the present invention will be more apparent to the expert of the art with the aid of the accompanying FIGS. 1 to 5 which are given by way of non-limiting example, and of which:

FIG. 2 is an axial section through the syringe during use;

FIG. 3 shows the syringe of FIG. 2 after use, with the needle retracted;

DETAILED DESCRIPTION OF THE PREFERRED EMBODIMENTS

Figure 1:
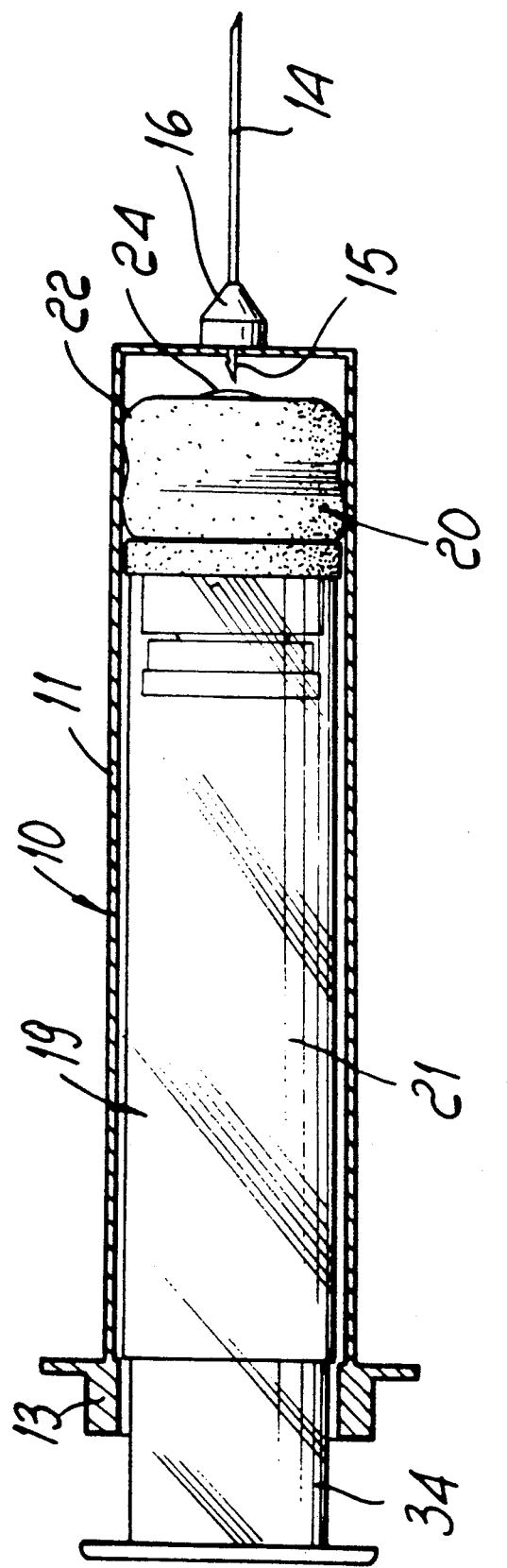
FIG. 1 is a partly sectional view of the syringe according to the invention.

In FIGS. 1 to 4 the reference numeral 10 indicates overall a hypodermic syringe constructed in accordance with the invention, and 11 indicates its cylindrical body, which is provided with a neck 12 and a guide ring 13.

The reference numeral 14 indicates a double-ended hollow needle 14 or metal cannula, provided with an engagement recess 15 and made rigid with the base 16 by a ring 18 or washer of a material which shears under a predetermined load; the base 16 is fixed to the neck 12 of the body 11.

The reference numeral 19 indicates overall the plunger which is slidable within the body 11 and is provided with a head 20 and a hollow shaft 21.

The head 20 of the plunger 19 is formed from a ring 22 of particularly elastic rubber, the channel 23 of which is closed by a disc 24 of easily shearable material.

The head 20 is fixed in a sealed manner to the shaft 21 of the plunger 19 by a plug 25 provided with a tube 26, which is forcibly inserted into the channel 23 of the rubber ring 22.

Figure 5:
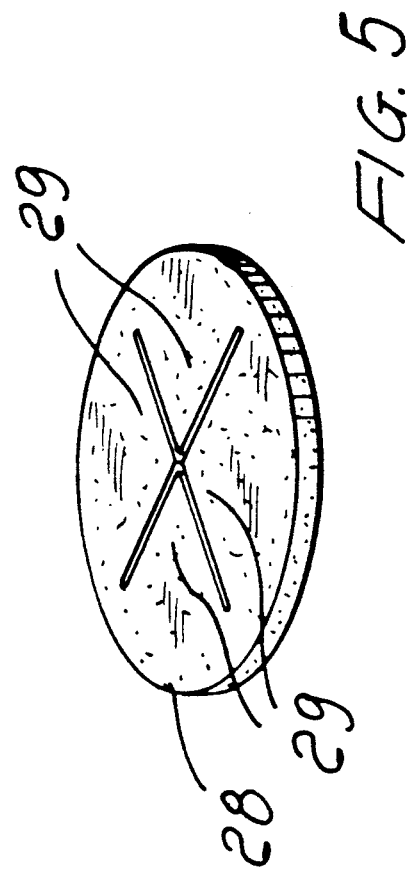
FIG. 5 shows a detail of the syringe of FIG. 2 in an enlarged scale.
Figure 4:
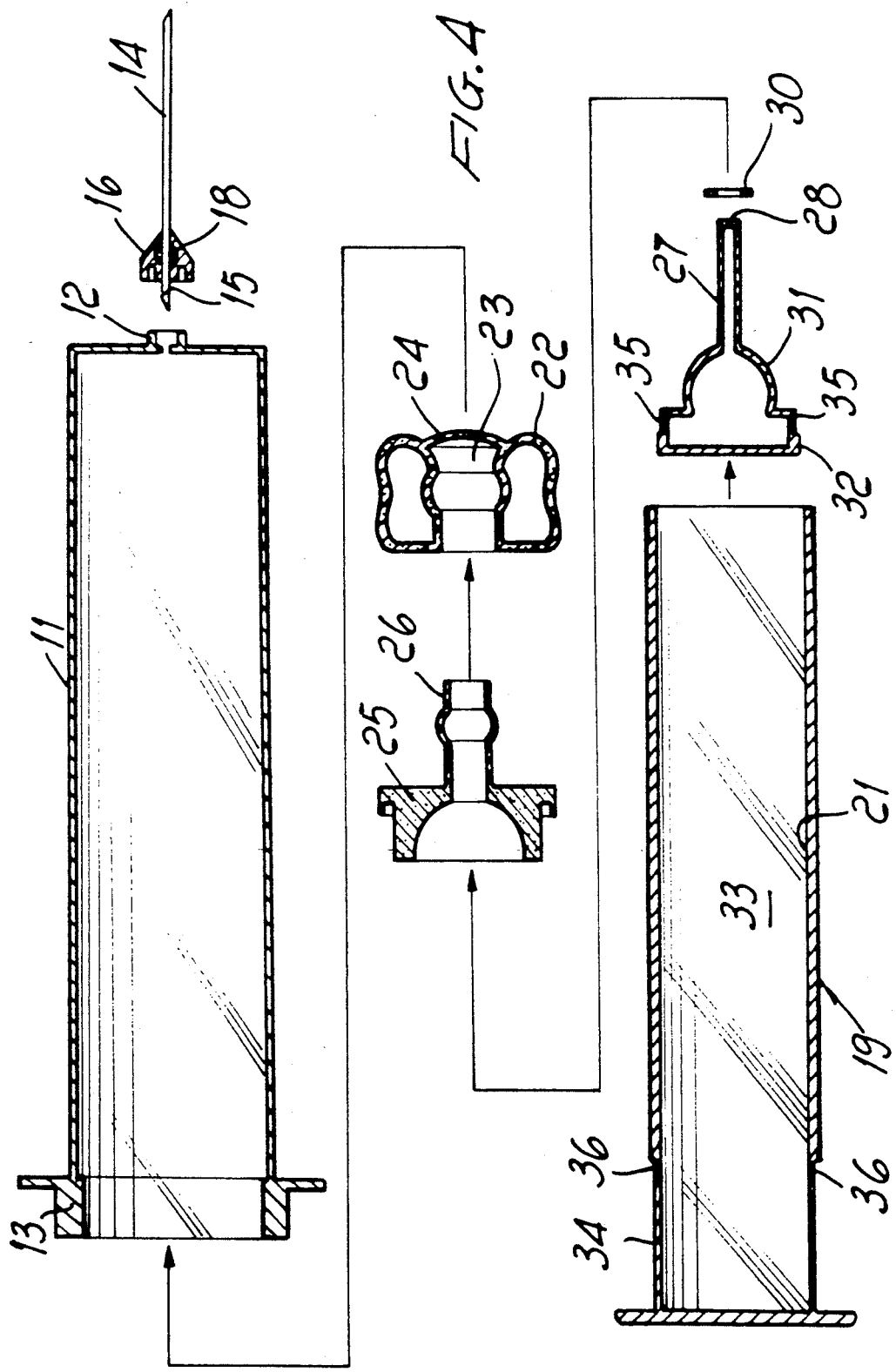
FIG. 4 shows the syringe of FIG. 2 during assembly.

The reference numeral 27 indicates an engagement rod with which a disc 28 provided with an X-shaped cut forming elastic flaps 29, visible in FIG. 5, is rigid.

The rod 27 is fixed to the tube 26 by a washer 30 of a material which shears under a predetermined load.

The rod 27 is rigidly connected by the hemispherical connector 31 to a piston 32, which is slidable in a sealed manner within the cylindrical chamber 33 of the hollow shaft 21.

The sealed sliding of the piston 32 in the chamber 33 is obtained either by the sealing contact between the contacting surfaces or, if necessary, by mounting a suitable seal ring on the piston 32.

A predetermined vacuum is provided in the chamber 33 of the hollow shaft 21.

The hollow shaft 21 has an end portion 34 of reduced outer diameter in order to reduce the resistance arising from contact with the inner wall of the guide ring 13 during the final part of the travel of the plunger 19.

The reference numeral 35 indicates two magnets incorporated in the piston 32 and 36 indicates two further magnets incorporated in the shaft 21 in proximity to the portion 34.

The pairs of magnets 35 and 36 have opposite polarities so that they attract each other.

When the syringe 10 is in use and the plunger 19 is about to finish its injection stroke, as shown in FIGS. 1 and 2, the disc 24 is lacerated by the inner point of the needle 14, the rod 27 then engaging the needle via the disc 28, the elastic flaps 29 of which engage the recess 15 in the needle 14.

The thrust exerted by the operator on the plunger 19 during the final part of the injection stroke to ensure that the liquid to be injected is completely expelled causes the washer 30 to break, thus releasing the rod 27 and the piston 32 from the plunger head 20. Under these conditions, under the action of the vacuum present in the chamber 33, the piston 32, the rod 27 and the needle engaged with it are sucked into the chamber 33, where they are retained by the mutual attraction of the pairs of magnets 35 and 36, as shown in FIG. 3.

The needle 14 cannot be reused and the syringe 10 is therefore rendered innocuous.

Constructional modifications of the syringe 10 fall within the scope of the present invention; for example the needle engagement device could be other than the rod 27 and disc 28; the vacuum chamber 33 could be in the form of a container housed in the hollow shaft 21.

The advantages of the present invention are the extreme ease of construction and assembly of the syringe, which in its external appearance hardly does not differ from the normal commercially available disposable syringes, but has the advantage that the fact that the needle disappears into its interior after use makes it innocuous and truly usable only once.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:
1. A hypodermic injection syringe comprising:
a generally cylindrical body;
a plunger slidable within said body, the plunger being provided with a hollow shaft defining an inner chamber;
one of a hollow needle and cannula;
first shearable means for connecting the one of a hollow needle and metal cannula to the body;
an engagement device connected to the plunger;
second means for connecting the engagement device to the plunger, the second means shearing under a determined load in response to an end of travel of said plunger, the engagement device becoming operationally connected to the one of a hollow needle and cannula at the end of travel of said plunger; and
a pneumatic actuator for drawing the one of a hollow needle and cannula into said chamber in the shaft of the plunger in response to shearing of the second means when the plunger reaches the end of travel.
2. The syringe as claimed in claim 1, wherein said pneumatic actuator is a vacuum type actuator.
3. The syringe as claimed in claim 1, further comprising a piston rigid with the engagement device, the piston being provided in the inner chamber of the hollow shaft of the plunger, the pneumatic actuator including vacuum pressure created in the inner chamber, the piston being slidable in the hollow shaft under sealed conditions.
4. The syringe as claimed in claim 1, wherein the engagement device comprises a rod rigid with a disc, the disc having an X-shaped cut forming elastic flaps engageable with a recess in the one of a hollow needle and cannula.
5. The syringe as claimed in claim 1, wherein the engagement device consists of a rod rigid with a disc, the disc having an X-shaped cut forming elastic flaps engageable with a recess in the one of a hollow needle and cannula.
6. The syringe as claimed in any one of claims 1 through 3, wherein the second means comprises a washer fixed to the engagement device and a head of the plunger, the washer being constructed of a material which shears under a determined load.
7. The syringe as claimed in claim 4, wherein the second means comprises a washer fixed to said rod and a head of the plunger, the washer being constructed of a material which shears under a determined load.
8. The syringe as claimed in claim 5, wherein the second means comprises a washer fixed to said rod and a head of the plunger, the washer being constructed of a material which shears under a determined load.
9. The syringe as claimed in claim 1, wherein the first shearable means comprises a ring constructed of a material which shears under a determined load, the first shearable means being rigid with the one of a needle and cannula and with a base fixed to the generally cylindrical body.
10. The syringe as claimed in claim 1, wherein the first shearable means consists of a ring constructed of a material which shears under a determined load, the first shearable means being rigid with the one of a needle and cannula with a base fixed to the generally cylindrical body.
11. The syringe as claimed in claim 1, wherein the piston and hollow shaft are provided with at least one pair of magnets, the magnets being arranged to attract each other.
12. The syringe as claimed in claim 3, wherein the piston and hollow shaft are provided with at least one pair of magnets, the magnets being arranged to attract each other.
13. The syringe as claimed in claim 1, wherein an end portion of the plunger has a reduced diameter to thereby reduce contact with an end of the cylindrical body.
14. The syringe as claimed in claim 13, wherein the plunger has a guide ring, the reduced diameter of the plunger end portion having reduced contact with the guide ring.
15. The syringe as claimed in claim 3, wherein an end portion of the plunger has a reduced diameter to thereby reduce contact with an end of the cylindrical body.
16. The syringe as claimed in claim 15, wherein the plunger has a guide ring, the reduced diameter of the plunger end portion having reduced contact with the guide ring.
17. The syringe as claimed in claim 1, wherein the second means shears in response to longitudinal movement of the plunger at the end of travel of the plunger.

* * * * *